United States Patent [19]

Ivie et al.

[11] Patent Number: 4,586,371
[45] Date of Patent: May 6, 1986

[54] APPARATUS FOR ADHESION TESTING OF COATINGS

[75] Inventors: Randall G. Ivie; William H. Thomason, both of Ponca City, Okla.

[73] Assignee: Conoco Inc., Ponca City, Okla.

[21] Appl. No.: 669,128

[22] Filed: Nov. 7, 1984

[51] Int. Cl.[4] .......................... G01B 21/00; G01N 3/08
[52] U.S. Cl. ...................................... 73/150 A; 73/827
[58] Field of Search ...................... 73/150 A, 827, 837; 156/155

[56] References Cited

U.S. PATENT DOCUMENTS

| | | | |
|---|---|---|---|
| 3,527,093 | 9/1970 | Sellers | 73/150 A |
| 3,577,775 | 5/1971 | Henderson | 73/150 A |
| 3,628,378 | 12/1971 | Regan, Jr. | 73/827 |
| 3,821,892 | 7/1974 | Saberg | 73/150 A |

FOREIGN PATENT DOCUMENTS

| | | | |
|---|---|---|---|
| 1455534 | 11/1976 | United Kingdom | 73/150 A |
| 642630 | 1/1979 | U.S.S.R. | 73/150 A |

*Primary Examiner*—Charles Frankfort
*Assistant Examiner*—W. Morris Worth
*Attorney, Agent, or Firm*—Stephen A. Littlefield

[57] ABSTRACT

An apparatus for applying a consistently perpendicular tension force to a dolly is provided for testing of the adhesive bond strength between a coating and a substrate. The tester comprises a ram passing through an axially centered opening in a dolly bonded to the coating. Piston and cylinder means are associated with the ram and the dolly so that pressure within the piston chamber formed thereby causes the development of a tension force within the dolly which is perpendicular to the coating being tested because of its coaxially centered orientation with respect to the ram.

9 Claims, 3 Drawing Figures

APPARATUS FOR ADHESION TESTING OF COATINGS

This invention relates to the art of materials testing and, more particularly, to an improved apparatus for the testing of coating adhesion to a substrate.

BACKGROUND OF THE INVENTION

For many applications, the adhesion of an exterior coating to a substrate is extremely critical. Whether the coating is for electrochemical protection such as an anodic coating of flame sprayed aluminum on a steel offshore structure or for providing passive protection such as a paint coating acting as a barrier against a corrosive environment, it is critical that the adhesion of the coating to the substrate be within well defined limits, depending on the application, in order to provide the requisite protection desired of the coating. Any protective advantage afforded by a coating is quickly lost when the coating separates from the substrate.

In order that the tests be reliably reproducible, it is essential that an adhesion tester apply purely tensile forces to the coating which are in a direction perpendicular to the coated surface. Any nonperpendicularly-directed forces can result in tearing of the coating and an inaccurate adhesion test reading.

U.S. Pat. No. 3,821,892 describes an apparatus for testing intercoat adhesion. A dolly is bonded to the test material and a tractive force is applied to the dolly which is located between a two-legged support, the legs bearing against the coated surface. While this apparatus is adequate for testing coatings on a completely flat surface, any localized irregularities within the span of the legs or any curvature in the part being tested can cause a coating to tear. U.S. Pat. Nos. 3,628,378 and 3,577,775 disclose apparatus of similar operation.

SUMMARY OF THE INVENTION

The present invention provides an apparatus and method for tensile adhesion testing of a coating to a substrate in which a force perpendicular to the tested material can be applied regardless of orientation, curvature or irregularities of the surface of the tested object.

In accordance with the present invention, an apparatus for measuring and testing of adhesive bonding of a coating to a substrate in a tensile mode comprises a dolly having an axially centered opening passing therethrough. The dolly further includes a bonding surface which substantially conforms to the surface of the coating to be tested. Bonding means for adhering the dolly bonding surface to the surface of the coating is provided, the bonding means having an adhesive bond strength in excess of the strength of the adhesive bond between the coating and the substrate. Also provided are ram means passing through the axially centered opening of the dolly, the ram means adapted for engagement against a centered portion of the coating surface which is bonded to the dolly. Piston means are attached to one of the ram and the dolly and cylinder means are attached to the other of the ram and the dolly for forcing the ram into pressure abutment against the coating surface and placing the dolly, the bonding means and the coating in tension.

Further in accordance with the invention, the aforementioned piston and cylinder means are hydraulically pressurized.

Still further in accordance with the invention, a method of testing the adhesive bond strength of a coating to a substrate in a tensile mode comprises providing a dolly having an axially centered opening therethrough and bonding the dolly to the coating with bonding agent having a bond strength in excess of the strength of the adhesive bond between the coating and the substrate. The coating is then cut through to the substrate around the outer circumference of the dolly so that only that portion of the coating bonded to the dolly will be tested. The dolly is then attached to piston and cylinder means which includes an axially centered ram, then passing through the axial opening of the dolly. Pressure is then applied to the piston and cylinder means to force the ram into pressure engagement with the coating and the pressure is monitored to the point at which the coating separates from the substrate.

It is therefore an object of this invention to provide a coating adhesion testing method and apparatus for measuring and testing the adhesive bond strength of a coating to a substrate in a tensile mode, the tension force being applied perpendicularly to the coating surface.

It is another object of this invention to provide an easily portable apparatus for the testing of coating adhesion to a substrate.

It is yet another object of this invention to provide a coating adhesion tester which may be easily adapted for use on a multiplicity of shaped structures.

BRIEF DESCRIPTION OF THE DRAWINGS

These and other objects of the invention will become apparent through a more detailed description of the invention and with reference to the accompanying drawings forming a part of this specification and in which.

DETAILED DESCRIPTION OF THE PREFERRED EMBODIMENTS AND DRAWINGS

Figures 1, 2, 3:
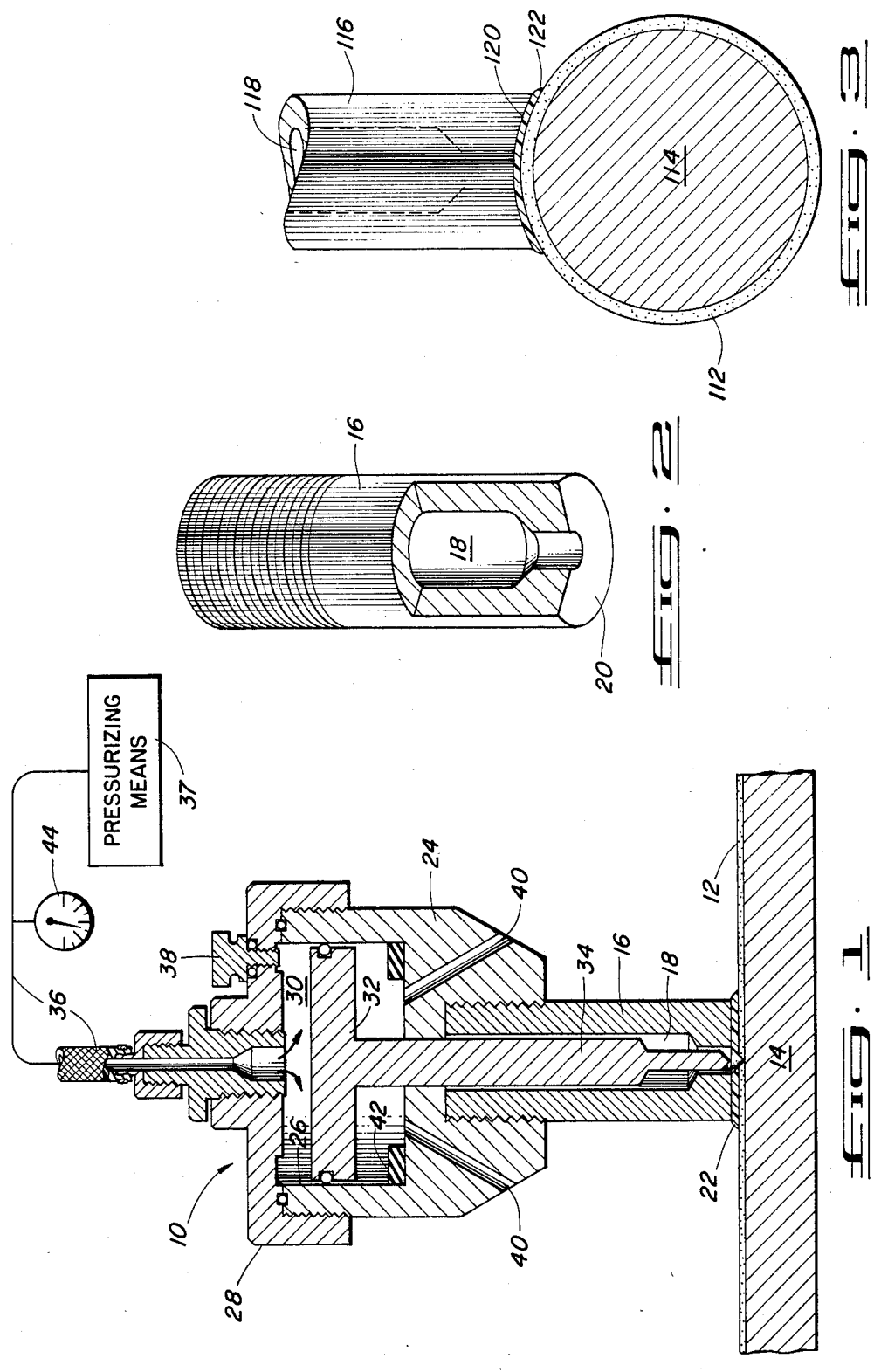
FIG. 1 is a schematic, cross-sectional view of the adhesion tester in accordance with the present invention.
FIG. 2 is a perspective view of a dolly used in a preferred form of the apparatus of the present invention.
FIG. 3 shows an alternative form of dolly in the testing mode of the present invention.

Referring now to the drawings wherein the showings are presented for the purposes of illustrating a preferred embodiment of the invention only and not for the purpose of limiting same, FIG. 1 shows an adhesion tester 10 in position for testing the adhesive bond between a coating 12 and a substrate 14. It will be understood that the coating 12 may be any type of coating such as a paint, a plastic laminate, or a metal coating applied by any of several processes such as flame spraying, electroplating, and the like. Similarly, the substrate 14 may be wood, a polymeric material, or metal. For purposes of illustrating a preferred embodiment, the coating 12 comprises a flame sprayed aluminum coating on a substrate 14 of steel.

In accordance with the invention, a dolly 16 having an axially centered bore 18 and a bonding face 20 (FIG. 2) is provided. The dolly 16 is bonded on its bonding face 20 to the coating 12 with bonding means such as a layer of cured epoxy or cyanoacrylate resin 22 extending between the surface of the coating 12 and the bonding face 20 of the dolly 16. Although the bonding means 22 is preferred to be an epoxy or cyanoacrylate for metal-on-metal coatings, any type of adhesive material may be used, the criteria for selection of a bonding means being that the adhesive strength of the bonding means 22 between both the coating 12 and the bonding face 20 of the dolly 16 exceeds the adhesive bond strength of the coating 12 to the substrate 14. As shown in the figures, the dolly is preferably cylindrical in form. It will be understood, however, that practice may dictate other forms which may be used so long as the bore 18 is axially centered in the dolly.

After the dolly 16 has been securely bonded to the coating 12, the dolly is attached to the tester assembly 24. A portion of the tester assembly 24 includes a cylindrical inner surface 26 and a cap 28 defining a piston chamber 30. A piston 32 is disposed within the piston chamber 30 and has an axially centered ram 34 attached thereto and extending outwardly of the tester assembly 24 through the axially centered opening 18 of the dolly 16 when mounted on the dolly. In order to separate the tested portion of the coating located immediately under the bonding face 20 of the dolly 16 from the remainder of the coating which could affect the tensional force required to pull the tested portion of the coating away from the substrate, the coating 12 is scored or cut around the outer circumference of the dolly 16. Any type of cutting means may be used for this purpose. This leaves the dolly 16 attached to a ring of coating of a known area suitable for quantative testing. Because of the pointed style of the ram 34, it is unnecessary to cut the inner circumference of the bore 18 of the dolly 16 in order to define the coating test area.

Pressurized fluid is admitted to the piston chamber 30 through a conduit 36 which is attached to some type of fluid pressurizing means 37 such as a hydraulic pump, an air pump, a pressurized fluid reservoir or the like. Various other features may be provided in the tester assembly 24 such as a bleed-off valve 38 for relieving pressure within the piston chamber 30 as well as various vent passages 40 for relieving pressure within the cylinder 26 on the side of the piston 32 opposite the piston chamber 30. Bump stops 42 may also be provided to limit the travel of the piston 32 and the ram 34.

In operation of the testing apparatus to test the tensile bond strength of the coating 12 through the substrate 14, pressurized fluid is admitted to the piston chamber 30 and the pressure is monitored by any common means such as a gauge 44. The pressure within the piston chamber 30 drives the piston 32 and its attached ram 34 into engagement with the surface of the coating 12. An increase in fluid pressure thus causes a tensional force to be developed in the dolly and, thereby, in the bonding means 22 and in the coating 12 as well. Because of the axially centered configuration of the ram 34 within the dolly 16, such tensional forces are consistantly applied perpendicular to the surface of the coating 12. At the point at which the tension forces in the dolly 16 the bonding means 22 and the coating 12 cause separation of the coating 12 from the substrate 14, the pressure monitored within the piston chamber 30 can be used to calculate the adhesive bond strength of the coating 12 to the substrate 14 which caused it to fail.

FIG. 3 illustrates an alternative form of dolly 116 which has a bonding face 120 which is curved to conform to the shape of the surface of a cylindrical member rather than a planar member as shown in the previous figures. The dolly 116 is bonded to the surface of a coating 112 on a substrate 114 utilizing bonding means 122 which may be any type as previously described with respect to the earlier figures. The dolly 116 has an axially centered bore 118 shown in phantom for accepting the ram 34 of the tester assembly 24 as previously described. It can be clearly seen that the axially centered nature of the ram 34 within the central bore 118 of the dolly 116 will cause the development of a perpendicular tensional force to test the adhesion of the coating 112 to the substrate 114.

EXAMPLE

The apparatus shown in FIGS. 1 and 2 was utilized to test the coating adhesion of a flame sprayed aluminum coating applied to a steel substrate. The dolly face had a surface area of 0.75 inch. The dolly was bonded to the surface of the flame sprayed aluminum coating using a cyanoacrylate adhesive designated CA-5 sold by 3M Company. The bond was allowed to cure for 24 hours although 80% of the bond strength may be reached after 1 to 2 hours. The CA-5 adhesive is rated at a tensile strength of up to 5,000 psi. After cutting of the coating to conform with the bonding face of the dolly, the coating testing apparatus was attached to the dolly and the pressure in the piston chamber was increased until a gauge pressure of 380 psi was noted at which point the bond between the coating and the substrate failed. Based on the size of the piston and surface area of the dolly, the calculated tensile loading and thus the coating adhesion strength at failure was 1,421 psi.

While the invention has been described in more limited aspects of the preferred embodiment thereof, other embodiments have been suggested and still others will occur to those skilled in the art upon the reading and understanding of the foregoing specification. It is intended that all such embodiments be included within the scope of this invention as limited only by the appended claims.

Having thus described our invention, we claim:

1. An apparatus for measuring and testing adhesive bonding strength of a coating to a substrate in a tensile mode comprising a dolly having an axially centered opening passing therethrough, said dolly having a bonding surface conforming to a surface of said coating; bonding means for adhering said dolly bonding surface to said coating surface, said bonding means having an adhesive bond strength in excess of a bonding strength of an adhesive bond between said coating and said substrate; ram means passing through said axially centered opening in said dolly, said ram means adapted for engagement against a centered portion of said coating surface bonded to said dolly; piston means attached to one of said ram and said dolly and cylinder means attached to the other of said ram and said dolly for forcing said ram into pressure abutment against said coating surface and for placing said dolly, said bonding means and said coating in tension, and means for determining said tension.

2. The apparatus as set forth in claim 1 wherein said dolly is cylindrical in form.

3. The apparatus as set forth in claim 1 wherein said means for determining said tension comprises a gauge for measuring pressure between said piston means and said cylinder means.

4. The apparatus as set forth in claim 3 further including means for providing hydraulic pressure to said piston and cylinder means.

5. The apparatus as set forth in claim 3 further including gas compressor means for providing compressed gas to said piston and cylinder means.

6. The apparatus as set forth in claim 1 wherein said bonding means is an epoxy resin.

7. The apparatus as set forth in claim 1 wherein said bonding means is a cyanoacrylate resin.

8. The apparatus as set forth in claim 1 wherein said bonding surface of said dolly is planar in form.

9. The apparatus as set forth in claim 1 wherein said bonding surface of said dolly is curved to conform with a curvature of a cylindrical-shaped substrate having said coating thereon.

* * * * *